United States Patent [19]

Fish et al.

[11] Patent Number: 5,126,276

[45] Date of Patent: Jun. 30, 1992

[54] METHOD FOR THE DETERMINATION AND MEASUREMENTS OF MORE THAN ONE UNKNOWN MATERIAL IN A SINGLE SURFACE OF A MULTIANALYTIC ASSAY

[76] Inventors: Falk Fish, 5 Kashani Street, Tel Aviv, Israel, 69499; Max Herzberg, Moshay Sataria, Israel, 73272; Menachem Ritterband, 25 E. Ben Yehuda Street, Rehovot, Israel, 70650

[21] Appl. No.: 113,395

[22] Filed: Oct. 19, 1987

Related U.S. Application Data

[63] Continuation of Ser. No. 675,439, Nov. 27, 1984, abandoned.

[51] Int. Cl.[5] .......................................... G01N 33/545
[52] U.S. Cl. ................................. 436/531; 435/7.92; 435/973; 435/975; 436/518; 436/519; 436/530; 436/541; 436/807; 436/808; 436/809; 436/810; 436/820; 422/56; 422/57; 422/58; 422/60; 422/61; 422/68.1; 422/69; 422/102
[58] Field of Search ............... 436/518, 519, 530, 531, 436/541, 807, 808, 809, 810, 820; 422/56, 57, 58, 60, 61, 68, 69, 102, 68.1; 435/7.92, 805, 810, 973, 975

[56] References Cited

U.S. PATENT DOCUMENTS

| | | | |
|---|---|---|---|
| D. 243,438 | 2/1977 | Bailey | D8/16 |
| D. 281,903 | 12/1985 | Duffy | D24/21 |
| D. 287,806 | 8/1888 | Parker | 172/375 |
| D. 538,146 | 4/1895 | Bailey | 172/375 |
| 1,902,705 | 3/1933 | Kee | 172/380 |
| 2,760,422 | 8/1956 | Wolf | 97/63 |
| 3,006,735 | 10/1961 | Jordan | 436/79 |
| 3,430,704 | 3/1969 | Alosi | 172/372 |
| 3,549,328 | 12/1970 | Kilburn | 422/56 |
| 3,552,925 | 1/1971 | Fetter | 436/169 |
| 3,763,515 | 10/1973 | Voss | 15/105 |
| 4,071,315 | 1/1978 | Chateau | 436/808 X |
| 4,142,402 | 3/1979 | Mattioli et al. | 73/61.2 |
| 4,144,452 | 3/1979 | Harte | 436/807 X |
| 4,147,752 | 4/1979 | Suovaniemi et al. | 436/810 X |
| 4,214,538 | 7/1980 | Druskin et al. | 111/95 |
| 4,225,575 | 9/1980 | Piasio et al. | 436/810 X |
| 4,237,096 | 12/1980 | Popoff et al. | 435/34 X |
| 4,276,259 | 6/1981 | Eible et al. | 436/820 X |
| 4,280,992 | 7/1981 | Sugiura et al. | 424/1 |
| 4,299,916 | 11/1981 | Litman et al. | 422/56 X |
| 4,308,028 | 12/1981 | Elkins | 422/56 X |
| 4,317,810 | 3/1982 | Halbert et al. | 424/12 |
| 4,657,869 | 4/1987 | Richards et al. | 422/102 |
| 4,822,565 | 4/1989 | Köhler | 422/57 |
| 4,891,321 | 1/1990 | Hubscher | 435/293 |

FOREIGN PATENT DOCUMENTS

| 8200058 | 1/1982 | World Int. Prop. O. | 436/501 |
|---|---|---|---|
| 8303677 | 10/1983 | World Int. Prop. O. | 422/58 |

*Primary Examiner*—Esther L. Kepplinger
*Assistant Examiner*—Carol A. Spiegel
*Attorney, Agent, or Firm*—Ostrolenk, Faber, Gerb & Soffen

[57] ABSTRACT

A solid phase immuno-assay system for assaying at least one analyte, in the form of a solid support having a plurality of receptors bound thereto. At least two of the receptors conjugate with the same analyte.

A reaction container comprising a plurality of longitudinally arranged individual compartments, and a longitudinally extending single compartment.

A card for assaying a plurality of samples for the same analyte, having a plurality of receptors for the analyte at different locations on the card.

A method of performing an assay for the same analyte in more than one sample, by providing a receptor for the analyte at more than a single location on a solid substrate; exposing each of the receptors to different samples; and developing each of the receptor locations to indicate the presence of the analyte in each of the samples.

21 Claims, 1 Drawing Sheet

METHOD FOR THE DETERMINATION AND MEASUREMENTS OF MORE THAN ONE UNKNOWN MATERIAL IN A SINGLE SURFACE OF A MULTIANALYTIC ASSAY

This application is a continuation of application Ser. No. 675,439, filed Nov. 27, 1984 now abandoned.

BACKGROUND OF THE INVENTION

1. Field of the Invention

The present invention relates to a method and apparatus for quantitatively and/or qualitatively assaying an analyte using a durable and storable recordation system.

2. Description of Material Information and Related Materials

Solid phase immuno-assays offer the most specific and sensitive methods for detecting and measuring an unknown material (analyte) in a given sample. While the actual use of these methods in the field is quite limited at present, various versions of solid phase assays have been developed and improvements have been proposed such that the earlier fluid phase immuno-assays (e.g. gel diffusion, precipitation, agglutination) will probably be replaced by a new generation of immuno-assays. Solid phase assays may be more complicated and require more elaborate and complicated technology, but they offer higher sensitivity and are better adapted for quantitative work. The present state of the art and the applicability of solid phase immuno-assays are extensively reviewed in U.S. Pat. Nos. 3,654,090 and 4,299,916.

Briefly, present methods are capable of measuring an unknown analyte provided it is either an antibody to a known antigen or an antigen, i.e., a material to which a specific antibody can bind.

Depending on the nature of the unknown, i.e., whether it is an antibody or an antigen, the specific counterpart (receptor) is affixed onto a solid surface such as the inner wall of a test tube, a dip-stick or beads. The analyte then binds to its solid phase receptor. The presence of the bound analyte and its quantity can then be determined by a labelled molecule (probe) which is either the analyte itself (competitive assay) or an antibody to the analyte ("sandwich" assay). The label can be radioactive (Radio Immuno-assay), enzymatic (Enzyme immuno-assay) or fluorescent (Fluorescence immuno-assay). The solid phase principle facilitates the separation of unbound labelled and unlabelled components of the assay system (antigens and/or antibodies).

Whilst the sensitivity of a solid phase immuno-assay can be tailored to the specific case, and specificity can be easily obtained, assays require certain improvements to make them more reliable, usable and portable. Thus, it would be desirable to:

a) Simplify and stabilize reagents, so that the assay components can be stored inexpensively and for long periods of time.

b) Provide an instantaneous, built-in quality control monitoring system for each of the steps involved since materials can become stale and steps may be improperly performed, thus affecting the final result.

c) Be able to perform differential diagnosis of infectious diseases where a plurality of unknowns can be screened in a single assay. Such a diagnosis would preferably be preformed using a single apparatus with a minimum of steps.

d) Be able to simultaneously assay a plurality of samples for the same unknown, without risk of cross-contamination.

e) Provide an apparatus with which untrained field staff may perform the assays and analyze the results obtained by visual inspection. To accomplish this the assay kits should be storage stable and simple to use. Such kits should include a minimal number of components and should lend themselves to easy filing and record keeping of the unknown, and standard values.

There is known in the art a card system adapted for sequential exposure to the various solutions of an assay procedure. The card itself may be made of polyvinyl, polystyrene, cellulose, nylon or glass. Depending upon the particular material selected, such a card may be suitable for storage for long periods of time.

Using a card configured in the known manner, individual samples to be assayed must be separately applied in a manner such that different samples do not contaminate one another. Even when samples are separately applied, because of the configuration of the card, the processing of the card may result in cross-contamination if more than one sample is applied to different parts of the card. As a result, the possibility of cross-contamination presents a serious obstacle to automated mass-processing. For this reason, the card lends itself more readily to multiple testing of a series of the same samples, rather than to simultaneously performing the same assay procedure on a plurality of samples from different subjects.

Furthermore, because of the configuration of the card, when different parts of the card must be separately processed, special precautions must be taken to prevent undesirable exposure. For example, depending upon the procedure, it may be desirable to subject the portion of the card having the control thereon to a different sequence of exposures. In such cases, special care must be taken to avoid exposure of the control portion, and the shape of the card may make such selective exposure somewhat awkward and difficult.

In addition to the above drawbacks, such cards would become more useful and commercially valuable if their results could be computerized. While results of such assays can, of course, always be manually inputted, it would be very useful if the results could be automatically read off of the card, and be stored in a retrievable manner which permits them to be readily associated with the particular subject from whom the sample(s) was (were) taken, together with any other pertinent information.

SUMMARY OF THE INVENTION

It is, therefore, an object of the invention to provide a solid phase immuno-assay system for assaying at least one analyte, which comprises a solid support having a plurality of receptors bound thereto, wherein at least two of the receptors conjugate with the same analyte. The solid support is most preferably in the form of a card.

When using a card, the card may have at least one tab protruding therefrom, with at least one of the receptors being applied to the tab. Most preferably, the card comprises a plurality of tabs protruding therefrom. Each of the tabs has at least one receptor for the same analyte, and may have a plurality of receptors for different analytes. Where a plurality of receptors are present on a single tab, each tab may have the same combination of different receptors.

A control may be provided by providing a reagent on at least one tab to control at least one of the receptor-analyte conjugate reactions.

To facilitate the use of the cards, at least one tab is provided with a pointed tip adapted to pierce a solid container seal.

The card preferably has identification means thereon to identify the source of analytes to which the card is exposed. The identification means may include a strip capable of visually displaying the source. The strip may be a surface adapted to be written on.

Alternatively, or in addition, the identification means may also comprise a magnetic strip which is readable by a computer means.

The tabs themselves may be positioned to extend to the same or different heights from the peripheral edge of the card.

The system may further include an optical measuring device for optically reading the chromogenic reaction occuring on the card. The optical measuring device may comprise fiber optics for individually reading each of the chromogenic reactions on the card, and may have computer means associated with the fiber optics to register the extent of reaction of the at least one receptor on the card. The identification means is readable by the computer means to be registered in association with the extent of reaction of the at least one receptor.

The card is most preferably formed of high impact polystyrene wherein at least one of the tabs has at least a portion thereof abraded to improve the adsorptive properties of the abraded portion for the receptor.

A reaction container having a plurality of individual compartments for receiving different samples therein is additionally contemplated as part of the system. The plurality of individual compartments are longitudinally aligned, and each of the individual compartments is preferably covered by a protective strip. The reaction container may further comprise at least one additional compartment extending parallel to the longitudinally aligned individual compartments. The additional compartment is also covered by a protective strip. The strip may be made of aluminum foil, and the tabs may be pointed to pierce the protective strip.

The invention is further directed to the reaction container alone which comprises a plurality of longitudinally arranged individual compartments, and a longitudinally extending single compartment. Each of the compartments is covered by a protective strip which, when broken, is capable of exerting a squeegee action on the portion of a card passing into and out of the compartment.

More broadly, the invention is directed to a card for assaying a plurality of samples for the same analyte, which card comprises a plurality of receptors for the analyte at different locations on the card. The card preferably includes a plurality of tabs extending longitudinally therefrom, with receptors being positioned on different tabs.

The invention is also directed to a method of performing an assay for the same analyte in more than one sample, by providing a receptor for the analyte at more than a single location on a solid substrate, exposing each of the receptors to different samples, and developing each of the receptor locations to indicate the presence of the analyte in each of the samples. The solid substrate is most preferably a card which comprises at least one, and preferably a plurality of tabs extending from one peripheral edge thereof.

The receptors are exposed to the samples by dipping the tabs within a reaction container having the samples contained therein. The reaction container has a plurality of longitudinally arranged individual compartments each containing a different sample, and the method comprises dipping each of the tabs into a different one of the longitudinally arranged individual compartments. The reaction container may further comprise a first additional longitudinally extending compartment containing a probe which conjugates with the analyte, and the method further comprises immersing all of the tabs into the longitudinally extending compartment, after immersion in each of the longitudinally arranged individual compartments. The card may be subsequently washed an then immersed in second and additional compartments.

The method includes the step of optically examining each of the tabs after immersion in the second compartment, preferably by means of a fiber optics system which includes optical fibers. The fiber optics system is associated with a computer means whereby the results of the optical examination are registered by the computer means, and stored in association with identification means on the card for identifying the samples to which the card is exposed. The identification means may be a magnetic strip readable by the computer means.

DESCRIPTION OF PREFERRED EMBODIMENTS

Figure 2:
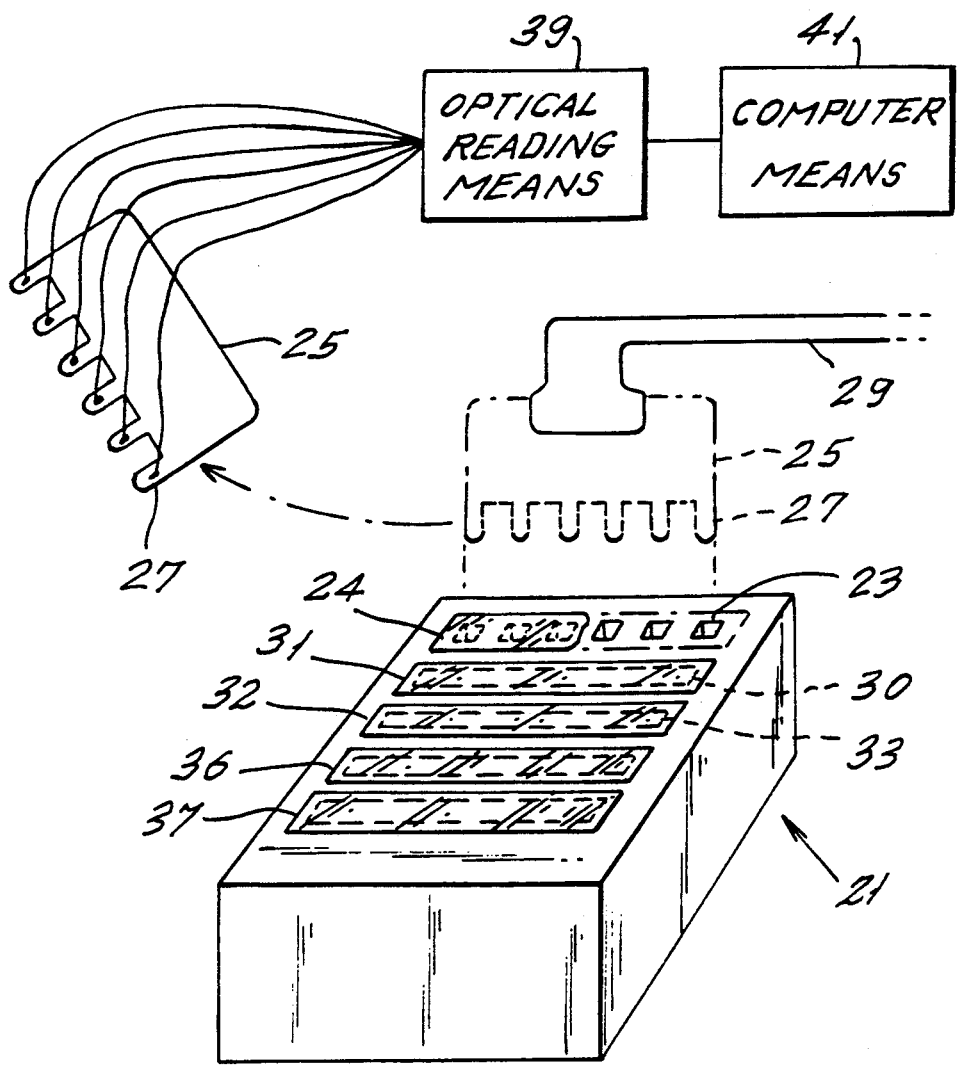
FIG. 2 illustrates a reaction container together with the optical measurment and computer means of the invention.

The invention relates to a system, method and apparatus capable of quantitatively and qualitatively analyzing an analyte in a manner which allows for improved quality control. The system of the invention is particularly valuable in that it lends itself very readily to automated exposure, processing and development.

The inventive assay system finds particular application when analyzing a plurality of different samples for the same, or different analytes. This is of particular interest where attempting to perform mass assays on groups of people or animals since as many as 12 or more samples may be simultaneously examined, by means of a single series of processing steps. By simple modification, the system even lends itself to multiple analyte assay, i.e., analyzing a particular sample for different analytes as may be the case when attempting to perform differential diagnosis.

Table I lists certain pathogenic bacteria and some of their specific virulence factors which may serve as antigens in the multi-analyte differential diagnosis of infectious diseases according to the invention. Table I is, of course, given by way of illustration only and is intended to be neither conclusive nor limiting:

TABLE I

| Bacteria | Virulence Factors |
| --- | --- |
| Bacillus anthracis | Edema producing toxin complex |
| Bordetella pertussis | Pertussis toxin |
| Corynebacterium diphtheriae | Diphtheria toxin |
| Escherichia coli | Heat labile enterotoxin |
| Staphylococcus | Exfoliating toxin; Enterotoxin |

TABLE I-continued

| Bacteria | Virulence Factors |
|---|---|
| aureus | |
| Streptococcus pyogenes | Erythrogenic toxin |

Differential detection is also useful with nucleic acid analytes. In this instance, a complementary receptor to be affixed to the substrate may be a complimentary strand of nucleic acid. Where a single-stranded nucleic acid is the analyte, it can bind to the receptor without any prior treatment. Where the analyte is a double-stranded nucleic acid, denaturation of the analyte is necessary before exposing the analyte to the receptors.

Table II lists certain instances in which differential detection of nucleic acids may be useful, thus enhancing the value of the technique of the present invention.

TABLE II

1. Viral infections—detection of latent infection (Herpes, varicella—zoster, EBV; encephalomyelitis: measles or Rubella (differential diagnosis).
2. Hereditary diseases—early diagnosis (in parents and fetus).

Table III is a partial list of groups of symptomatically similar diseases in which the detection of antigen and/or antibody, can be helpful in differential diagnosis. Of course, the listing is not intended to be limiting or all-inclusive.

TABLE III

| Syndrome | Etiologic Agents |
|---|---|
| Pharyngitis & Tonsilitis (sore throat) | Strep. pyogenes, C. diphteria N. gonorrheae, N. mengitidis H. influenza B, Adenovirus, Herpes, Coxackie, Epstein Barr Virus |
| Otitis Media | Strep pneumoniae, H. influenza, Strep. pyogenes, Staph aureus, Proteus, Pseudomonas |
| Influenza | Various hemagglutinin and cialidase types |
| Stomatitis | Differential diagnosis between Herpes and others needed to avoid use of steroids |
| Meningitis | H. influenza, N. meningitidis, Strep. pneumoniae, S. aureus, Cryptococcus neoformans, Herpes simplex |
| Parotitis | Mumps, Influenza, Parainfluenza, Staph. aureus, Strep. viridans, pneumococci, E. coli, Haemophilus |
| Pertussis | B. pertussis, B. parapertussis, Adenovirus |
| Pneumonia | Strep. pneumoniae (= Pneumococcus) Strep. hemolyticus, Strep. pyogenes, Staph. aureus, N. meningitidis, Klebsiella pneumoniae, E. coli, P. aeruginosa, H. influenza, Mycoplasma pneumoniae, Legionella pneumophila, Misc. viruses |
| Diarrhea | Shigella sp., Salmonella sp., E. coli, Cl. perfrigens, Vibrio parahemolyticus, Vibrio cholera, Campylobacter fetus, Yersinia enterocolitica, Rotavirus |
| Urinary Tract Infections | E. coli, Proteus sp., Aerobacter sp., Strep. faecalis, Staph. aureus, Pseudomonas sp., others |

The inventive technique also permits the concomitant assay of both antigens and antibodies, on a single substrate from the same sample. Such a technique is useful in the diagnosis of infectious diseases where an excess of antibody signifies the convalescent stage of the illness, and signifies that chemotherapy is no longer indicated.

The following are examples of antigen-antibody systems in which both members may be assayed according to the invention.

TABLE IV

Newcastle Disease
Whooping cough
Measles
Influenza
Pneumonia

As was noted above, other analytes may be detected by detecting the following resultant receptor-analyte couples using the technique of the present invention: hormones and their receptors; various drugs, chemicals and vitamins, and their receptors; neurotransmitters and opiates and their receptors; enzymes and their substrates, and toxins and their receptors.

For purposes of the invention, the term "receptor" is used in its broadest sense and merely refers to any substance capable of complexing and/or affixing to an analyte in a manner which allows for subsequent use or treatment of the affixed material, preferably in a manner which facilitates its identification, and/or quantification, e.g., commonly used receptors include proteins.

The system of the invention is useful in assaying for the presence of virulence factors, e.g., exotoxins, adherence factors, hemolysins; nucleic acids; hormones; drugs; chemicals; vitamins; neurotransmitters; opiates; enzymes; toxins; etc.

It is a preferred aspect of the invention that the assay be performed using a solid support having a plurality of the same receptors thereon, each of which is capable of binding the same analytes thereto. The solid support is insoluble in the solution being analyzed and is preferably sufficiently flexible to provide for ease of manipulation.

The support of the invention may assume a variety of configurations and may be round and flat, card-like, e.g., square or rectangular an flat, tubular, a rod, a stick, cylinder, etc. The support used may obviously be any material capable of maintaining its general configuration during use.

A preferred configuration according to the invention is a support in the form of a sheet which may be circular, but which is most preferably rectangular. Such a substrate may be formed of polyvinyl, polystyrene, or high-impact polystyrene, although other materials may quite obviously be used. The shape of the support, as well as the material of which it is made, may quite obviously vary depending upon the circumstances of use.

According to a most preferred aspect of the invention, the card is provided with at least one, and preferably a plurality of tabs extending from a peripheral edge thereof. Each of the tabs is provided with at least one receptor thereon, with two or more of the tabs having the same receptor thereon, thereby allowing the simultaneous assay of a plurality of samples for the same analyte(s).

The different receptors may be bound to the support in a variety of ways. Immunoglobulins (antibodies) and many protein antigens, will spontaneously bind to various plastics e.g., polystyrenes and polyvinyls, as well as other polymeric materials, e.g., celluloses and nylons, as well as to glass fibers. High-impact polystyrene can be an especially convenient solid support which allows for good binding of protein antigens and low background activities at later stages of the assay. Additionally, the support may be formed of a material which is coated with a layer of another material or polymer such as nitrocellulose for purposes of increasing the surface area of the support.

Single-stranded nucleic acids also bind spontaneously to the materials recited in the previous paragraph. Double stranded nucleic acids do not bind to any significant extent to such surfaces such that when working with such materials, two possible approaches are available.

According to a first approach, the double stranded nucleic acid is bound by means of a cationic polymer such as poly-L-lysine to the support (according to a technique disclosed in Fish and Ziff, Arth. Rheum. 24:534, 1981).

According to a second technique, the nucleic acid is bound covalently after the support itself has been activated. Various techniques are available for activating supports such as cellulosic paper for such purposes and such papers are now available commercially from various suppliers such as SCHLEICHER and SCHULL, or ORGENICS LTD.

One suggested technique for activating celluloses is the use of cyanuric chloride, which had previously not been adapted to flat surfaces such as paper and which is found to be most convenient and economical. This same method can be used for smoother surfaces such as celluloid, cellulose acetate, cellulose nitrate and agarose films.

Polysaccharides are similar to double-stranded nucleic acids in their inability to bind spontaneously to polymers. They can, however, be attached to plastics by means of another charged polymer, e.g., poly-L-lysine, or they could be covalently bound to proteins by periodate oxidation, and Schiff's base formation, before attempting to adsorb them onto plastics. Again, the cyanuric chloride activation technique may be used to bind polysaccharides, as well, to cellulosic materials.

Low molecular weight materials usually cannot be bound directly to a solid support and, therefore, must first be bound to a spacer molecule, e.g., a protein, before binding to the solid support. U.S. Pat. No. 4,299,916, the disclosure of which is herein incorporated by reference, reviews the various possibilities of binding a receptor to a solid phase support.

High-impact polystyrene is a particularly preferred substrate material. It has been found that the adsorptive qualities of high-impact styrene can be unexpectedly improved particularly for proteins and nucleic acids if the surface of the substrate is roughened or abraded.

The receptors which are selectively attached at prearranged locations to the support will, quite obviously, vary as a function of the analytes being assayed. Thus, for a given analyte, or group of analytes, the receptor selected will differ. Where the analyte is an antigen, the receptor would be the specific antibody. Where the analyte is an antibody, the receptor will be the corresponding antigen. When the analyte is a nucleic acid, the receptor is the complementary nucleic acid.

Once the receptors have been bound onto the support, such as by absorption and/or adsorption, particularly when the receptor is a protein, the support may be washed in a dilute detergent to prevent any further binding of protein. In certain instances, "blocking" or "saturation" of the surface by another protein in solution, unrelated to the bound protein, may be required such as is disclosed in U.S. Pat. No. 4,299,916.

Where the support surface has been chemically activated, inactivation by appropriate chemicals and under certain conditions may be required. For example, when cyanuric chloride-activated cellulose is used as the support, inactivation with 1M ethanolamine at pH 8.0 is preferred.

Depending upon the activity of the receptor, special precautions may be necessary to protect the receptor during storage prior to use. Additionally, depending upon the receptor, special drying techniques may be required.

With the receptor adhering onto the support, the analyte-containing sample can be applied to the support by various techniques, depending upon the quantities available, the source of the sample, and the shape of the solid support.

The treated substrate is contacted with the analyte-containing liquid for a sufficient time and under appropriate conditions to permit the various analytes to bind to their respective receptors. Depending on the circumstances, such application may take the form of dipping the substrate into a solution containing the analytes, swabbing the substrate with the solution, etc.

Figure 1:
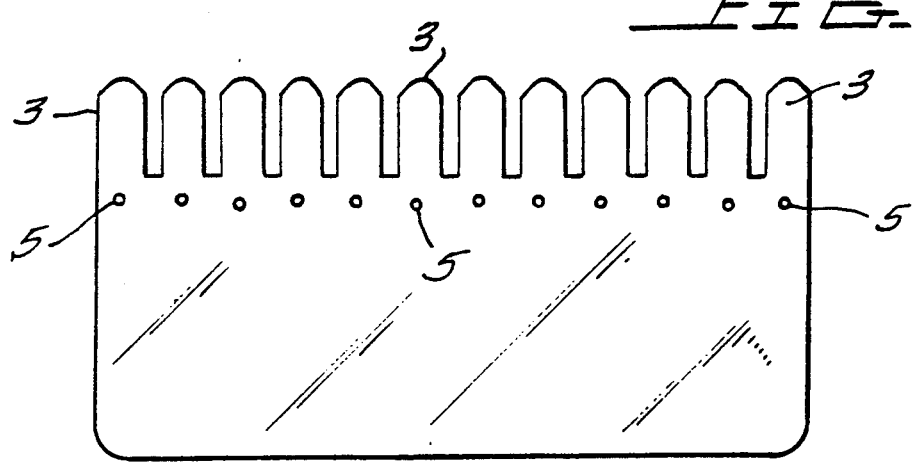
FIG. 1 illustrates a card according to the invention.

When using a card-like support 1 of the type shown in FIG. 1, the tabs 3 of the cards may be dipped into the sample, if it is liquid, or the sample itself can be streaked or swabbed across the appropriate spaces on the solid support. The card is coated with control spots for monitoring the various parameters of the assay and standard spots 5 which provide a standard curve for purposes of comparison with the receptor-treated areas. The locations of the spots vary according to their function, i.e., certain spots are intended for serial exposure to all solutions, while others are not.

Other analyte-receptor pairs may require other conditions. Solid or semi-solid samples such as bacterial cultures, tissues, etc., will require some degree of mechanical and/or enzymatic homogenization before applying them to the receptor-coated substrate surface.

During this stage of the procedure, the physicochemical conditions for each analyte-receptor pair should be optimized. This means that for antigen-antibody interactions, for example, an isotonic environment with an above neutral pH would be ideal. Incorporation of the same detergent used to wash the solid phase after receptor binding may actually increase the specificity of the reaction and reduce unwanted background reactivity at later stages.

Of course, sufficient time must be allowed for interaction between the analyte and the receptor. The physicochemical conditions may be altered such that the contact time may be shortened, if desired, such as, for example, by higher temperature, or inclusion of some polymers in the interaction mixture, e.g., 4% polyethylene glycol 6000.

Once analyte is bound onto the substrate receptors, the support is again washed to remove unwanted excess. The subsequent washing procedure is of utmost importance as is the case with any solid phase immunoassay. This is particularly true of the multi-analyte system of the invention. The wash procedure may include a detergent, e.g., BRIJ 35T, or another suitable detergent.

The wash procedure of the invention may be facilitated by utilizing a squeegee effect which wipes off excess liquid from the support.

The washed, analyte-containing support is then developed, such as by exposure to a probe-containing solution, to quantitatively and/or qualitatively establish the presence of the analytes. This may be achieved such as by development of a color reaction, a radioactive immunoassay, either competitive or non-competitive, a sandwich technique, etc.

The identity of the various analytes may be determined simply by observing their locations on the tabs since they will be adhering to receptors which have been positioned at pre-determined locations on the support. Thus, the mere positive reaction at a given tab location is indicative of the presence of a suspected analyte.

The washed support may be developed in the office, under field conditions, or in the laboratory.

The probe which is used to detect the bound analyte is normally a labelled receptor to the analyte in question. The probe will specifically attach to the receptor-bound analyte and allow detection and quantitation by virtue of a label associated therewith.

In immunoassays for an antigen, the probe is preferably the same as the solid support-bound receptor. In immunoassays for antibodies where the solid support receptor is the antigen, the probe is preferably an antibody against the immunoglobulin-type of the analyte antibody, e.g., labelled anti-human immunoglobulin would be the probe for human antibodies.

The probe antibodies may be labelled by radioactive isotopes or by enzymes by any of a number of well known techniques such as are described in U.S. Pat. Nos. 3,654,090 and 4,099,916, the disclosures of which are hereby incorporated by reference thereto.

For purposes of the present invention, enzymes which form an insolubilized color reaction at the various probe locations such as peroxidase, glucose oxidase, or beta-galactosidase may be used.

Although radioactive labels can alternatively be employed in the present invention, this results in some complication and slowdown of the detection method. Thus, for purposes of the invention, enzymatic techniques are preferred.

In certain cases it is desirable to use an unlabelled probe, and then to detect the probe with a labelled material, e.g., antibody to the probe. Such a technique may increase sensitivity at the expense of higher background reactions. This technique is also well known in the art, see for example, Hale and Randle, Biochem. J. 88:137, 1963, and need not be further described at this point.

In the case of a double-stranded nucleic acid analyte bound to a support, one of three general approaches may be used to obtain a probe.

APPROACH I

Anti-double-stranded DNA (anti-dsDNA) antibodies are isolated from systemic Lupus Erythematosus patients or animals with comparable diseases. Anti-single stranded DNA antibodies must first be removed by appropriate absorption techniques. Anti-dsDNA which remains can be labelled first and used directly to identify the analyte materials with which it binds to form a duplex. Alternatively, unlabelled duplex-bound anti-dsDNA antibodies may be detected subsequently with a labelled anti-immunoglobulin antibody while the duplex is bound onto the support.

APPROACH II

The analyte samples are first chemically modified so as to add an immunoreactive group to them without substantially damaging their stereostructure. One simple chemical modifier is picryl sulfonate which introduces a THP (trinitrophenyl) group into the amines of the nucleic acid analyte. The production of anti-TNP antibodies is a well known procedure in the art, such as is disclosed in Nowotny, "Basic Exercises in Immunochemistry", Springer Verlag, New York 1969. Another method for introducing an immunoreactive group into a nucleic acid is described by Poverenney et al., J. Immunol. Methods, 16:313, 1979. Labelled antibodies to the nucleic acid modifiers are then used as probes to detect the bound analytes.

APPROACH III

Nucleic acid molecules, identical to the receptor, may be labelled in vitro with immunoreactive groups such as described according to the second technique above, or by other techniques. These molecules are then mildly hydrolyzed to produce smaller pieces of nucleic acids which serve as probes. These probes are then allowed to anneal with parts of the bound analytes under mild denaturing conditions (60° C., 20-40% formamide). After annealing, the probes are detected by antibodies to the immunoreactive groups as described immediately above.

When using enzyme labels, a color reaction is developed to detect the bound enzyme-labelled-probe. According to the invention, a preferred technique for developing an enzyme color reaction comprises using a peroxidase-labelled probe, or using any other enzyme which converts a soluble dye into an insoluble dye which precipitates at the site of the bound enzyme.

According to another alternative, the colorless dye may also be insoluble before conversion to develop a color reaction. The use of a dye which is capable of being rendered insoluble is extremely important according to the invention since the location of the dye must conform to the location of the enzyme-labelled antibody probe if accurate identification is to be made possible.

One known technique for the localization of peroxidase is described by Buckel and Zehelein (Gene 16:149, 1981) as part of an assay to detect a protein on the surface of bacterial colonies. The method involves touching a flat solid support (carrying the enzyme-labelled probe) to the surface of a gelatin-based gel, containing the substrate and dye system for peroxidase. While this method is applicable to the conditions of a research laboratory, it may not readily lend itself to a kit designed to be used under field conditions.

Thus, it is yet another aspect of the invention that the system of the invention may include an enzyme color development substrate system which is designed for improved storage and field use. Hydrogen peroxide, the substrate of the enzyme label, is extremely labile and will undergo spontaneous lysis when in aqueous solution. Therefore, the following substrate systems are provided according to the invention:

(a) a cellulose based sheet which may be made of paper, cellulose membrane, etc., and which is impregnated with a gelatin-based fluid gel, at high temperature, containing the dye and buffer, and allowed to dry spontaneously or by lyophilization. Before use, the sheet is dipped into a solution of hydrogen peroxide in 50% methanol and then touched to the peroxidase enzyme-carrying solid support for color development.

(b) The same technique is used as in (a) but the paper itself is also impregnated with glucose oxidase. Before use, the paper is dipped into a dilute aged glucose solution (2% concentration). Hydrogen peroxide will be generated by the glucose oxidase and will render the reagent kit more stable.

(c) The reagent mixture for the dye-substrate is completely dry and may comprise:
   (1) a gelling agent which requires no heating to be activated, e.g., instant starch, sodium alginate;
   (2) a gelling initiator, where applicable, e.g., calcium ions for alginate;
   (3) glucose oxidase and glucose (as a source for hydrogen peroxide);
   (4) a dye;
   (5) a buffer system; and
   (6) an effervescent (not required but may be used as a chemical means for improving mixing and facilitating reaction).

Using this technique, the substrate mixture is suspended in an appropriate solvent such as water, or water and alcohol. The tabs of the flat solid phase support are dipped into the suspension and immediately taken out. The color reaction will develop in the gel which adheres to the flat surface of the support. After development of the color, the gel may be washed or wiped off the solid support.

Quite obviously, each of the above detection techniques may also be used with a probe which is labelled with glucose oxidase. In this case, glucose and peroxidase should be included in all substrate-dye mixtures.

The method for attaching the substrate-dye mixture to the solid phase support described above may lend itself to other enzyme labels, making appropriate changes in substrate compositions.

An alternative dye generation system is described in Bio Rad Price List J, 1984 (p. 169) and available commercially from that company or other suppliers of chemicals (e.g. Sigma). The system is based on 4-chloro-1-naphthol as the electron donor chromogenic substrate. In its reduced (colorless) form the material is soluble in alcohol:water mixtures. In the presence of peroxidase and hydrogen perioxide the material forms a blue-black precipitate. Using this technique, a probe which is labelled with peroxidase or glucose oxidase thereon can be detected by dipping the tabs of the solid support on which the probe is affixed into a solution containing 4-chloro-1-naphthol and peroxide (in the case of a peroxidase labelled probe) or glucose and peroxidase (in the case of glucose oxidase labelled probe).

The peroxidase-glucose oxidase enzymes may be substituted by alkaline phosphatase as the label. In this case, the chromogenic system is described in the literature (Turner, J., Immunol. Methods, 63: 1-6, Bode et al., J Virol. Methods, 8:111-121, 1984).

EXAMPLE 1

Chromogenic Substrate-Chloro-Naphthol Chromogenic Mixture for Peroxidase

Mix 1 volume of 3 mg 4-chloro-1-naphthol per ml. methanol with 5 volumes of a solution of 0.018% hydrogen peroxide in Tris buffered saline (20 mM Tris. HCl, 500 mM NaCl, pH 7.5). This mixture provides a complete chromogenic mixture for peroxidase. Filter paper can be impregnated with the mixture as above, and rehydrated prior to use as noted above.

QUANTITATIVE ANALYSIS

Additionally, the present invention provides for quantitative or semi-quantitative analysis of analyte presence using visual observation, or relatively inexpensive optical measurement apparatus.

Quantitative analysis of the various analytes is achieved by coating the support with a range of analyte concentrations for each suspected analyte, and then exposing these control regions of the substrate to the same conditions as the remaining portions of the substrate (subsequent to affixation of the sample analyte onto the support). By comparison of the results over the entire support it is possible to obtain a good semi-quantitative reading as to the presence of a particular analyte. This is done by comparing the color of the developed receptor regions with the developed regions of control analyte bound on the card. The control appears as spots 5 in a predesignated area of the solid support (see FIG. 1). Such a determination may be made by visual or instrument inspection.

QUALITY CONTROL

A problem inherent in any immunological assay kit is the fact that it contains many reagents and involves many reactions, each of which may go wrong and yield a false-negative result. The present invention provides an optional system for monitoring some or all of the components of the assay for proper activity.

Antigen Analyte

Quality control may be provided by assaying while performing the following tests, each represented by a spot on the solid support:

(1) Control is provided for the activity of the dye-substrate system by means of enzyme (where an enzyme system is being used) bound individually to the support to ensure that the dye-substrate is properly operating.

(2) Control for the activity of the probe, i.e., the enzyme-labelled antibody to the antigen analyte, is achieved by binding analyte to the solid support and observing the activity of the analyte upon exposure to the enzymatic probe-containing solution. A negative result indicates that the enzymatic probe solution may have lost activity. Alternatively, or in addition, the tabs may be coated in selected regions with avidin, and the enzyme-labelled probe is correspondingly labelled with biotin such that the probe can bind to the tabs on the support. This should provide a positive result, upon chromogenic development, if the enzyme-dye substrate system is properly functioning.

(3) Control for establishing that all incubation times throughout the procedure have been sufficient is achieved by employing a non-related analyte-receptor system. The control analyte is either incorporated into the sample solution or is supplied in a separate container to be applied to the solid support at the time the sample is applied. The probe solution also contains probe for the control analyte such that non-cross-reacting control analyte reactions are subject to the same handlings and incubations as the analyte reactions which are the subject of the procedure.

Antibody Analyte

The quality control system in an assay for an antibody analyte may include the following tests:

(1) A control for the activity of the dye-substrate system in the form of an enzyme bound to the solid support, e.g., using the avidin-biotin technique referred to above.

(2) A control for the activity of the enzyme-labelled anti-immunoglobulin probe wherein immunoglobulin derived from the same species of the analyte antibody, is bound to the solid support surface.

(3) Control for sufficient incubation times is provided by a non-cross-reacting antigen bound to the solid support. If an anti-serum to the antigen, derived from the same species is available, then it may be included as a separate control solution or be incorporated into the sample-solution. Where an anti-serum is unavailable, as occurs with human samples, TNP-bovine serum Albumin may then be used as a support-bound antigen since for dietary reasons, many individuals carry antibodies to bovine antigens. Additionally, hydrophobic hapten TNP (trinitrophenyl) is able to bind a detectable amount of immunoglobulin from normal serum (See Fish and Ziff, J. Immunol. 128:409, 1982). In any case, batches of blood bank plasma or serum can be screened for the presence of such antibodies. Those demonstrating a high enough response may be incorporated as a separate control serum, or incorporated into the sample solution.

In both of the above examples, a slight problem exists as to Control 1 in each case. The shelf life of the support-bound enzyme may be shorter than the enzyme in the probe. In that case, when the assay is being performed the control enzyme can be tagged with a biotin label which will affix the entire molecule to an avidin molecule, previously bound to the solid support. Thus, as part of the assay procedure the control enzyme may be affixed to the support, such that shelf storage ceases to be a problem.

EXAMPLE 2

Control for the Dye-System

Horseradish peroxidase conjugated to goat immunoglobulin (e.g. commercially available from Miles, or prepared according to Nakane and Kawasi, J. Histochem. Cytochem. 22:1084, 1974) is diluted 1:100 in phosphate buffered saline pH 7.5 or in 1M sodium bicarbonate pH 9.6. The solution is applied to a polystyrene support surface. After 30-60 minutes at room temperature (e.g. 25° C.), the polystyrene is washed in 0.85% NaCl. The polystyrene support is then dipped in a 1% w/v solution of BSA (Bovine Serum Albumin CRG-7, Armour) for 30 minutes and washed first in 0.85% NaCl, and then in water. Alternatively, a solution of the pure enzyme itself (0.01–0.1 U/ml) in 0.15M ammonium bicarbonate containing 1% BSA is applied to the polystyrene surface and allowed to dry.

The support-bound enzyme is then exposed to the substrate-dye system.

EXAMPLE 3

Control for the Activity of the Probe

When the analyte is an antibody, serum obtained from healthy young specimens of the same species producing the antibody analyte is diluted 1:1000 in phosphate buffered saline (PBS) or 1M sodium bicarbonate pH 9.6. The solution is applied to a polystyrene support, allowed to incubate for 30 minutes at room temperature, and washed off with 0.85% NaCl containing 0.1% BRIJ 35T.

Alternatively, immunoglobulin, isolated from whole serum can be employed. In this instance a 10 microgram/ml solution of the immunoglobulin in PBS or 1M sodium bicarbonate is used.

For an analyte which is an antigen, the control antigen is attached to the solid support in a manner similar to the above.

(a) With protein antigens, e.g., immunoglobulin, bacterial toxins (pertussis toxin, cholera toxin, tetanus toxin), albumins, the antigens are diluted to 10 microgram/ml and applied to the surface.

(b) With nucleic acids and polysaccharides binding to plastic surfaces may be facilitated by a polycationic linking polymer such as poly-L-lysine. A suggested procedure is given in Fish and Ziff, Arth. Rheum. 24:534, 1981.

EXAMPLE 4

Control for Sufficient Exposure Time and Proper Handling (a) For an antigen analyte: As a non-cross-reactive antigen one of the following may be chosen: egg albumin, keyhole limpet hemocyanin (KLH) and any other antigen which is not related to the analyte-receptor system. An antiserum to the control antigen produced in the same animal species, in which the receptor-antibody to the tested analyte is being produced, is diluted 1:1000 in PBS or 1M sodium bicarbonate pH 9.6 and applied to the solid support at the appropriate space to serve as the receptor. The control analyte is added to the tested analyte or to the first wash solution at a concentration of 50–500 ng/ml. A control probe will contain an enzyme-labelled antibody to the control antigen. The control probe is added to the test probe solution at the same concentration.

(b) For an antibody analyte: one of the antigens above 5(a) is applied to the surface (10 ug/ml in PBS or 1M sodium bicarbonate pH 9.6) in the appropriate place. The antiserum to the control antiserum is added in a 1:1000 dilution to the measured analyte-antibody or to the first wash. The remainder of the procedure is then performed, as before.

Nucleic Acids

When detecting and identifying nucleic acid sequences, the same types of controls may be employed, i.e.:

(1) Control for the substrate-dye system, as was previously described.

(2) Control for the labelled probe. A double-stranded nucleic acid or chemically modified nucleic acid can be attached to the solid support at the appropriate location on the tabs.

(3) Control for hybridization time and conditions by using non-cross hybridizing nucleic acid pairs.

STANDARD REFERENCE CURVE

The multi-analyte test described until this point may be used qualitatively. The system will thus provide a positive or negative answer as to the existence of a particular antigen, antibody or nucleic acid. However, "standard spots" can be added to the solid support to obtain quantitative information. The standard spots 5 are all positioned above the tabs (FIG. 1) so that the standard spots can be selectively exposed to only certain solutions during the assay procedure, and are not exposed to the sample solutions.

In the semi-quantitative mode, each standard spot has a progressively increasing analyte or enzyme concentration and the standard spots will yield, after full development of the assay, a scale of color densities, each corresponding to a different amount and/or concentration of analyte.

For more quantitative results, the entire control portion of the solid support may be scanned utilizing a suitable optical densitometer. An exact standard curve can then be constructed and the exact quantities of analyte can be more precisely determined.

Alternatively, or in addition, additional standard or control spots may be utilized, and will now be described.

PROCEDURE 1

A different amount of enzyme is attached to the card above the tabs. After complete development with dye, each spot will demonstrate a different color density. The spots may be correlated by the manufacturer with different amounts of analyte and this information may be included with the test kit.

PROCEDURE 2

A different amount of avidin is attached at each spot. The enzyme-labelled probe is also tagged with biotin which will enable it to bind to the avidin on the standard spot. Afterward, the procedure is identical to that of Procedure 1, based upon a guide provided by the manufacturer.

PROCEDURE 3

For assay systems where the analyte is an antibody, the standard spots may contain different amounts of an immuno-globulin, derived from the same species, donating the antibody. The labelled probe (an anti-immunoglobulin) will then bind to these spots according to the amount of immunoglobulin attached and will yield different color densities. These densities are once again compared to a standard comparison chart provided by the manufacturer.

PROCEDURE 4

Receptor-analyte combinations may be employed as in Procedures 2 and 3, provided they do not interfere with the tested analytes or their receptors.

PROCEDURE 5

For an enzyme containing polysaccharide in its molecule (e.g. horse radish peroxidase) the plastic surface can be coated with different quantities of a lectin (a molecule which binds carbohydrates) such as Con A. The use of this approach, however, should be limited only to those cases where the analyte itself is devoid of carbohydrates.

PROCEDURE 6

Different concentrations of antibody produced against the enzyme, originating in an animal species identical to the donor of the antibody in the enzyme-antibody probe.

EXAMPLE 5

Example of Procedure 1

An enzyme-immunoglobulin conjugate prepared according to Nakane and Kawasi (J. Histochem. Cytochem. 22:1084, 1974) is diluted 1:100, 1:200, 1:400, 1:800, 1:1600; 1:3200, in PBS pH 7.4 or in 1M sodium bicarbonate pH 9.6. Each dilution is applied on the plastic support at its predetermined spot. Following a 30–60 minutes incubation at room temperature, the whole plastic sheet is washed in 0.85% NaCl with 0.1% BRIJ 35T.

EXAMPLE 6

Example of Procedure 2

The antibody is labelled with biotinyl groups using commercially available reagents (e.g. from Sigma Chemical Co., St. Louis, Mo., U.S.A.) or as described in the professional literature (Guedson, Ternyck and Avrameas, J. Histochem. Cytochem. 27:1131, 1979). It is then conjugated to peroxidase by the method of Nakane and Kawasi, J. Histochem. 22:1084. Avidin obtained from commercial sources (e.g., Sigma) is dissolved to 10 micrograms/ml in PBS pH 7.4 or 1M sodium bicarbonate pH 9.6. This solution is serially diluted 1:1 to obtain the points of the standard curve. Each dilution is then applied onto the plastic support at its predetermined spot. Following a 30–60 minute incubation, the plastic support is washed as above.

EXAMPLE 7

Example of Procedure 3

Either one of the following two approaches can be employed:

(a) Using whole serum as the source of immunoglobulin: The unprocessed serum is diluted 1:1000 in PBS pH 7.4 or 1M sodium bicarbonate pH 9.6 and then is 1:3 serially diluted in the same buffer. The various concentrations are then applied as in Examples 5 and 6.

(b) Using separated immunoglobulin: immunoglobulin is derived from whole serum by ammonium sulphate precipitation (e.g., Fish, Witz and Klein, Clin. Exp. Immunol. 16:355, 1974). A solution of 10 microgram/ml in PBS pH 7.4 or 1M sodium bicarbonate pH 9.6 is prepared (immunoglobulin content is determined by OD at 280 and 260 nanometers as described by Layne, Methods Enzymology 3:447, Academic Press, 1966). The immunoglobulin solution is serially diluted 1:1 in the same buffers. The procedure is then continued as above with respect to Examples 5 and 6.

EXAMPLE 8

Example for Procedure 4

Basically similar to control procedure for sufficient exposure times and reaction conditions, employing non cross-reactive receptor analyte system (see above example 5). However, in this case the receptors are reacted with various concentrations (e.g., 20 ng/ml–1000 ng/ml) of the analyte where the analyte is a protein antigen. If the analyte is an antibody, whole antiserum dilutions are placed on the solid support. The dilutions depend on the particular batch of antiserum and must be determined beforehand by testing serial 1:2 dilutions from 1:10 up to 1:10000.

EXAMPLE 9

Example for Procedure 5

Concanavalin A (obtainable from: Sigma, GIBCO, Miles) is dissolved to 10 micrograms/ml in PBS pH 7.4 or 1M sodium bicarbonate pH 9.6. It is then further serially diluted 1:2 in the same buffer. The individual dilutions are placed on the plastic support as described in Example 5.

EXAMPLE 10

Example for Procedure 6

Antiserum against the enzyme, e.g., horse radish peroxidase, is either obtained commercially or produced in the appropriate animal (rabbit, goat, chick) by repeated immunizations (100 micrograms enzyme in 1 ml 0.85% NaCl emulsified with 1.0 ml complete Freund's adjuvant (GIBCO or Difco) injected i.d. followed 3–4 weeks later with 200–500 ug peroxidase emulsified as above in incomplete Freund's adjuvant). The antiserum is applied to the plastic surface as described in procedure 3a above (Example 7).

APPARATUS

An assay according to the invention may be performed using a variety of apparatus. Since the various reagents are applied to a card, the assay may be performed in conjunction with apparatus of the type shown in FIG. 2, which includes a container 21 having no lid which is divided into a plurality of longitudinally individually arranged compartments for receiving sample solution to be assayed. Each of compartments 23 constitutes a separate and individual well which is filled to a level such that insertion of tabs 27 of card 25 therein results in contact between the solution and the tabs. Because each of the wells is separated by a wall, and by virtue of the configuration of the card, when the tabs are inserted into the wells, the card cannot be immersed deeply enough so as to bring the control spots into contact with the sample solution. There is, therefore, no possibility of contaminating the control spots with the various samples, nor of contaminating the samples with one another.

Each of compartments 23 is covered by a foil 24 which when broken exerts a squeegee effect on the tabs being inserted and withdrawn from compartments 23.

The card tabs may be inserted within compartments 23 by means of a mechanical arm 29. Prior to or after insertion within compartments 23, the source of the various samples to which the tabs are exposed may be identified on the card simply by writing or typing the information at an appropriate location on the card which is treated to permit writing if necessary. According to another embodiment, before or after immersion in compartments 23, a magnetic strip (not shown) on the card is encoded with the appropriate information as to the source of the samples.

After removal from compartments 23, the tabs are then immersed into compartment 30 through the foil 31 where the tabs are exposed to an appropriate wash solution. This compartment is not separated by walls into individual compartments, such that the card may be dipped further into the compartment such that appropriate control and standard spots on the body of the card are exposed to the wash solution. The tabs are then removed through the foil which wipes off excess liquid, and are then re-immersed into compartment 32 through foil 33 wherein the control spots and tabs are exposed to a probe solution.

Once again, the card is washed in compartment 36, and finally developed in compartment 37 by exposure to a chromogenic substrate or the like.

The results on the tabs are then read by means of optical reading means 39, and the results are ultimately registered and recorded by computer means 41.

In order to provide for filling each of the compartments, an orifice (not shown) covered with a rubber septum through which liquid may be injected into the various compartments. The liquid may be the bath itself, or a dehydrated form of the bath which is merely rehydrated by the user prior to use.

By covering each of the compartments with foil, the broken foil serves to indicate whether immersion in that compartment has occurred as yet. The foil may additionally include instructions thereon and may be numbered to facilitate manual processing, even by relatively untrained personel. The foil may be aluminum foil, or may be made of a rubber sheet, cellulose, etc. As noted above, the foil additionally serves to wipe excess liquid off of the card as it is inserted and removed from each compartment.

The various compartments shown in FIG. 2 are given by way of example only, and are not intended to be limiting in any way. Thus, additional compartments for washing, etc. may also be provided in a similar manner. The reagents for each stage are loaded into the corresponding compartment and the compartments are arranged in the order they are used.

For the reasons noted above, it may be desirable to expose different spots on the card to different combinations of solutions, or to fewer solutions than other dots on the card. This may be achieved in a number of different ways.

In one technique the various tabs have different heights, relative to the peripheral edge of the card. In this instance, different tabs will submerge to different extents in compartments filled to different levels with solution. Thus, in certain instances short tabs will not be exposed to a particular solution in which other tabs are immersed.

According to another embodiment of the invention, the compartments themselves have different depths which, therefore, prevent total immersion of the card up to the peripheral edge of the card itself. Thus, only the tab portions for example are immersed in the shallower compartments, e.g. sample containing compartments, while the remaining deeper compartments are allow for immersion until the peripheral edge of the card where control or standard spots may be located.

Although the invention has been described with reference to a flat card, it may likewise be adapted to other forms of solid support such as flat sticks or rods. Additionally, although the invention has been described with reference to particular means, materials and embodiments, it is to be understood that the invention is not limited to the particulars disclosed and extends to all equivalents within the scope of the claims.

What is claimed is:

1. An analytical system for simultaneously assaying a plurality of samples for at least one analyte, comprising:
   (a) a device comprising a solid, planar comb support in the form of a card, said support having a plurality of planar tabs extending from a peripheral edge of said support in a spaced manner and capable of being immersed into individual compartments of a multi-compartment reaction container wherein
      (i) a least two tabs each comprise a defined area containing at least one receptor capable of specifically binding said at least one analyte,
      (ii) at least one tab comprises an assay monitoring control immobilized thereon,
      (iii) at least two tabs each comprise a standard of known analyte concentration immobilized thereon;

and wherein said support further comprises identification means thereon to identify said samples; and
(b) a multi-compartment reaction container comprising:
  (i) a plurality of individual, longitudinally aligned first compartments collectively capable of simultaneously receiving all of the tabs of device (a), each first compartment capable of receiving only one of the tabs, and
  (ii) at least one second compartment capable of simultaneously receiving all of the tabs of device (a), the longitudinal axis of each second compartment disposed parallel to the longitudinal axis of the longitudinally aligned first compartments;
and wherein each first and second compartment is sealed with a protective strip.

2. The system of claim 1 wherein each tab comprises a defined area containing at least one receptor capable of specifically binding the same analyte.

3. The system of claim 2 wherein the receptors on each tab are the same.

4. The system of claim 1 wherein each tab further comprises a pointed tip adapted to pierce the protective strip of the compartment into which it is immersed.

5. The system of claim 1 wherein said identification means comprises a strip capable of visually displaying the source of the analyte.

6. The system of claim 5 wherein said strip is a surface adapted to be written on.

7. The system of claim 5 wherein said identification means comprises a magnetic strip which is readable by a computer means.

8. The system of claim 1 wherein at least two of said tabs are of different heights relative to said peripheral edge from which said tabs extend.

9. The system of claim 1 wherein all of said tabs are of the same height relative to said peripheral edge from which said tabs extend.

10. The system of claim 1 further comprising (c) an optical measuring device.

11. The system of claim 10 wherein said optical measuring device comprises fiber optics.

12. The system of claim 11 further comprising (d) computer means associated with said fiber optics for recording the results of the assay.

13. The system according to claim 1 wherein said solid, planar comb support is formed of high impact polystyrene.

14. The system of claim 13 wherein a portion of at least one tab has an abraded area carrying said at least one receptor thereon.

15. The system according to claim 1 wherein the protective strip covering each compartment, when broken, is capable of exerting a squeegy action on the portion of the tabs passing into and out of the compartment.

16. The system according to claim 1 wherein said protective strip comprises aluminum foil.

17. The system according to claim 1 wherein at least one of said tabs comprises a plurality of receptors positioned thereon and wherein each of said receptors is at a different height on said tab relative to the peripheral edge from which said tab extends.

18. The system according to claim 1 wherein the depth of each said first compartments is less than the distance from the peripheral edge of each said tab having an assay monitoring control immobilized thereon to the control immobilized thereon.

19. A reaction container adapted for use in a system for performing simultaneous multiple assays on a plurality of samples for at least one analyte without cross contamination among said multiple assays,
  said reaction container comprising a plurality of individual, longitudinally aligned first compartments capable of simultaneously receiving all of the tabs of a device comprising a solid, planar comb support in the form of a card and a plurality of planar tabs extending from a peripheral edge of said support in a spaced manner, each first compartment capable of receiving only one of said tabs, and at least one second compartment capable of simultaneously receiving all of the tabs of said device, the longitudinal axis of said second compartment disposed parallel to the longitudinal axis of said plurality of longitudinally aligned first compartments, and each of said first and second compartments covered by a protective strip which, when broken, is capable of exerting a squeegy action on the portion of said tabs passing into and out of said compartments.

20. The reaction container of claim 19 wherein said protective strip is aluminum foil.

21. The reaction container of claim 19 wherein at least one of said first compartments has a depth which is different from the depth of the other first compartments.

* * * * *